(12) United States Patent
Chu et al.

(10) Patent No.: US 9,254,128 B2
(45) Date of Patent: *Feb. 9, 2016

(54) RE-SHAPEABLE MEDICAL DEVICE

(75) Inventors: Michael S. H. Chu, Brookline, MA (US); Alfred P. Intoccia, Jr., Amherst, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 943 days.

This patent is subject to a terminal disclaimer.

(21) Appl. No.: 13/455,552

(22) Filed: Apr. 25, 2012

(65) Prior Publication Data

US 2012/0209304 A1    Aug. 16, 2012

Related U.S. Application Data

(63) Continuation of application No. 10/384,682, filed on Mar. 10, 2003, now Pat. No. 8,187,288.

(51) Int. Cl.
    *A61B 17/04*     (2006.01)
    *A61B 1/005*     (2006.01)
    *A61B 17/00*     (2006.01)
    *A61B 17/29*     (2006.01)

(52) U.S. Cl.
    CPC ............ *A61B 17/0469* (2013.01); *A61B 1/0058* (2013.01); *A61B 17/0482* (2013.01); *A61B 2017/00867* (2013.01); *A61B 2017/00946* (2013.01); *A61B 2017/2905* (2013.01); *A61B 2017/2927* (2013.01)

(58) Field of Classification Search
    CPC ........... A61B 17/0469; A61B 17/0482; A61B 1/0058; A61B 2017/00946; A61B 2017/2905; A61B 2017/00867

USPC ......................................... 606/139, 144–148
See application file for complete search history.

(56) References Cited

U.S. PATENT DOCUMENTS

| 4,762,128 A | 8/1988 | Rosenbluth |
| 5,037,433 A | 8/1991 | Wilk et al. |
| 5,047,039 A | 9/1991 | Avant et al. |

(Continued)

FOREIGN PATENT DOCUMENTS

| WO | 9622738 A1 | 8/1996 |
| WO | 01/34240 A2 | 5/2001 |

OTHER PUBLICATIONS

International Search Report for International Application No. PCT/US2004/006557 dated Aug. 20, 2004, 8 pages.

(Continued)

*Primary Examiner* — Katherine Rodjom

(57) ABSTRACT

A medical device enables a user to bend it into a shape to suit a specific patient need or to orient efficiently the medical device for use. The medical device includes an elongate member, a mechanism, and an actuator. The mechanism is disposed at the distal portion of the elongate member. The actuator is at least partially disposed within the elongate member and coupled to the mechanism for actuating the mechanism relative to the elongate member. The elongate member is capable of being bent into a shape by the user and of retaining the shape during use. The shape may include multiple bends, in multiple directions, as needed for an application. Thereafter, the elongate member is capable of being bent into a second shape by the user and of maintaining the second shape during use.

22 Claims, 7 Drawing Sheets

(56) References Cited

U.S. PATENT DOCUMENTS

| | | |
|---|---|---|
| 5,271,543 A | 12/1993 | Grant et al. |
| 5,275,614 A | 1/1994 | Haber et al. |
| 5,281,234 A | 1/1994 | Wilk et al. |
| 5,312,430 A | 5/1994 | Rosenbluth et al. |
| 5,330,491 A | 7/1994 | Walker et al. |
| 5,391,174 A | 2/1995 | Weston |
| 5,417,699 A | 5/1995 | Klein et al. |
| 5,417,702 A | 5/1995 | Hempel |
| 5,439,467 A | 8/1995 | Benderev et al. |
| 5,441,507 A | 8/1995 | Wilk |
| 5,480,407 A | 1/1996 | Wan et al. |
| 5,501,692 A | 3/1996 | Riza |
| 5,527,322 A | 6/1996 | Klein et al. |
| 5,562,688 A | 10/1996 | Riza |
| 5,613,974 A | 3/1997 | Andreas et al. |
| 5,643,292 A | 7/1997 | Hart |
| 5,662,666 A | 9/1997 | Onuki et al. |
| 5,700,272 A | 12/1997 | Gordon et al. |
| 5,716,367 A | 2/1998 | Koike et al. |
| 5,746,754 A | 5/1998 | Chan |
| 5,755,728 A | 5/1998 | Maki |
| 5,766,187 A | 6/1998 | Sugarbaker |
| 5,779,719 A | 7/1998 | Klein et al. |
| 5,810,849 A | 9/1998 | Kontos |
| 5,814,054 A | 9/1998 | Kortenbach et al. |
| 5,855,585 A | 1/1999 | Kontos |
| 5,868,760 A | 2/1999 | McGuckin, Jr. |
| 5,876,411 A | 3/1999 | Kontos |
| 5,895,395 A | 4/1999 | Yeung |
| 5,897,563 A | 4/1999 | Yoon et al. |
| 5,902,311 A | 5/1999 | Andreas et al. |
| 5,910,148 A | 6/1999 | Reimels et al. |
| 5,928,250 A | 7/1999 | Koike et al. |
| 5,951,575 A | 9/1999 | Bolduc et al. |
| 5,964,782 A | 10/1999 | Lafontaine et al. |
| 5,984,948 A | 11/1999 | Hasson |
| 5,993,464 A | 11/1999 | Knodel |
| 5,993,467 A | 11/1999 | Yoon |
| 6,004,332 A | 12/1999 | Yoon et al. |
| 6,048,351 A | 4/2000 | Gordon et al. |
| 6,096,051 A | 8/2000 | Kortenbach et al. |
| 6,129,741 A | 10/2000 | Wurster et al. |
| 6,143,005 A | 11/2000 | Yoon et al. |
| 6,161,543 A | 12/2000 | Cox et al. |
| 6,161,643 A | 12/2000 | Bober et al. |
| 6,174,280 B1 | 1/2001 | Oneda et al. |
| 6,224,614 B1 | 5/2001 | Yoon |
| 6,280,460 B1 | 8/2001 | Bolduc et al. |
| 6,346,111 B1 | 2/2002 | Gordon et al. |
| 6,387,075 B1 | 5/2002 | Stivland |
| 8,187,288 B2 * | 5/2012 | Chu .................. A61B 17/0469 606/144 |
| 2001/0023352 A1 * | 9/2001 | Gordon .............. A61B 17/0469 606/144 |
| 2002/0045908 A1 | 4/2002 | Nobles et al. |
| 2003/0009177 A1 | 1/2003 | Middleman et al. |
| 2003/0045900 A1 * | 3/2003 | Hahnen ........... A61B 17/07207 606/205 |
| 2003/0139752 A1 | 7/2003 | Pasricha et al. |
| 2003/0236549 A1 * | 12/2003 | Bonadio ................ A61B 17/29 606/205 |

OTHER PUBLICATIONS

Written Opinion for International Application No. PCT/US2004/006557, 8 pages.

Communication pursuant to Article 94(3) EPC for EP Patent Application 04716941.2, mailed on Mar. 18, 2015, 5 pages.

* cited by examiner

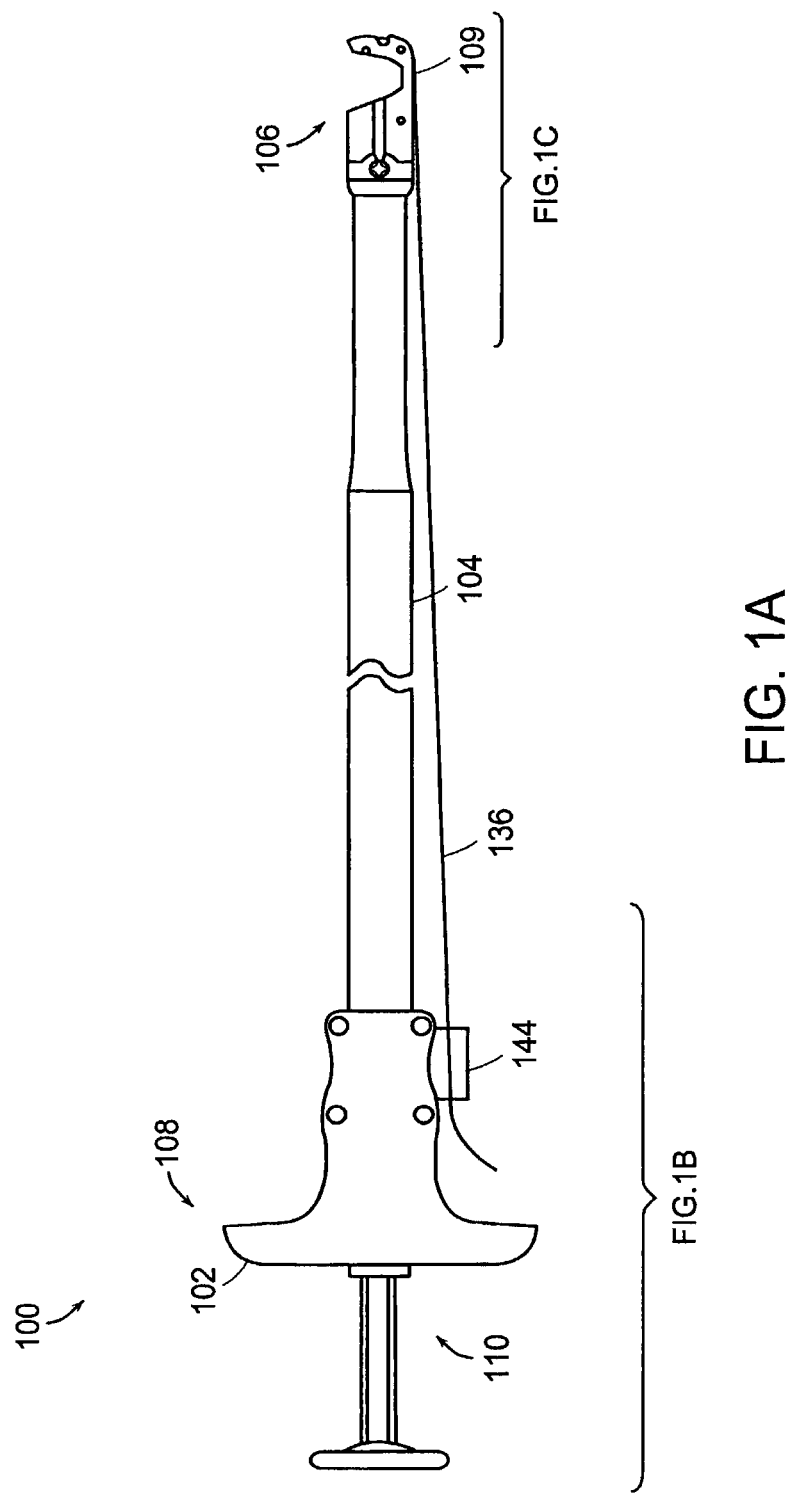

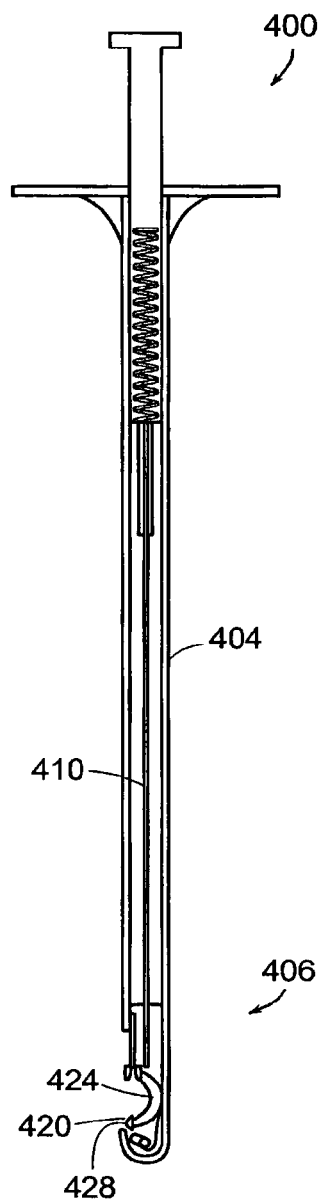 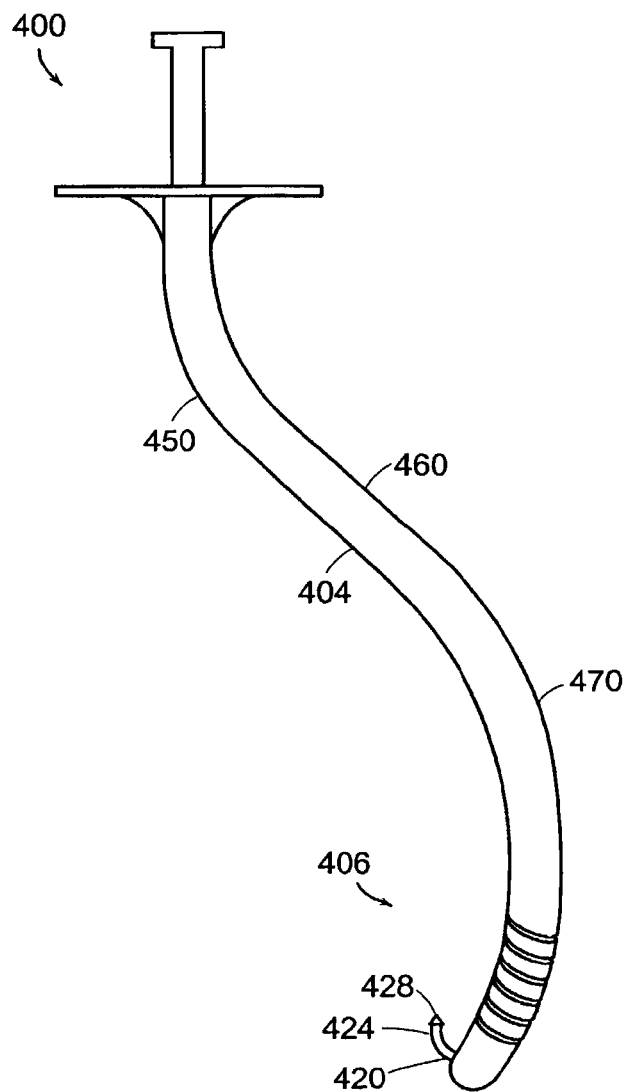
FIG. 4A
FIG. 4B

RE-SHAPEABLE MEDICAL DEVICE

RELATED APPLICATION

This application is a continuation of U.S. application Ser. No. 10/384,682, filed on Mar. 10, 2003, the contents of which are herein incorporated by reference in its entirety.

TECHNICAL FIELD

The invention relates to devices and methods for accessing remote areas within the body and performing surgical procedures therein.

BACKGROUND INFORMATION

For many surgical procedures, it is necessary to make a large opening in the human body to expose the area that requires surgical repair. There are instruments available that allow for viewing certain areas of the human body through, for example, a natural body opening or a small puncture wound, and thus avoid the need for making such large openings. These instruments, called endoscopes, can be used in conjunction with specialized surgical instruments to detect, diagnose, sample, and repair areas of the body that previously required open surgery to access.

Some surgical instruments used in endoscopic procedures are limited by the way they grasp tissue, cut tissue, apply a suture, or recapture the needle and suture. Furthermore, many surgical instruments are complicated and expensive to use due to the numerous parts and/or subassemblies required to make them function properly. Suturing, in particular, remains a delicate and time-consuming aspect of most surgeries, including those performed endoscopically.

In addition, many of the instruments used in endoscopic procedures are limited by the manner in which they access the areas of the human body in need of diagnosis, sampling, treatment, or repair. In particular, the instruments may not be able to access tissue or organs that are located deep within the body or that are in some way obstructed. The instruments used in endoscopic procedures typically have a rigid shaft, and do not allow the user to contour the shaft for a more efficient orientation to reach the location of diagnosis, sampling, treatment, or repair. Instruments with various shaft configurations have been introduced to accommodate specific applications. Thus, a user's inventory of instruments may include a number of rigid shaft instruments for various applications.

SUMMARY OF THE INVENTION

The invention generally relates to a medical device for performing a surgical procedure, such as removing a mass of tissue, grasping a mass of tissue, or passing a suture through tissue. Specifically, in one embodiment, the invention is directed to a medical device that can be bent by a user into a shape to suit a specific patient need or to efficiently orient the distal portion of the device to reach the location of use. The shape may include multiple bends, in multiple directions, as needed for a particular application. The medical device maintains the shape during use. Thereafter, the medical device is capable of being bent into a second shape by the user to suit another specific patient need or to efficiently orient the distal portion of the device to reach the location of another use; the device is further capable of maintaining the second shape during use.

In one aspect, the invention is directed to a medical device including an elongate member, a mechanism, and an actuator. The elongate member is capable of being bent into a shape by a user and of retaining the shape during use. The mechanism is an arrangement of one or more parts connected and/or operated to perform a task, such as diagnosis, sampling, treatment, or repair. The mechanism is disposed at a distal portion of the elongate member. The actuator is at least partially disposed within the elongate member and coupled to the mechanism for actuating the mechanism relative to the elongate member.

In another aspect, the invention relates to a medical device including an elongate member, an adapter, and an actuator. The elongate member is capable of being bent into a shape by a user and of retaining the shape during use. The adapter is disposed at a distal portion of the elongate member for coupling to a mechanism. The actuator is at least partially disposed within the elongate member and is capable of coupling to the mechanism and of actuating the mechanism.

In yet another aspect, the invention relates to a suturing instrument including an elongate member, a head, a needle carrier, and an actuator. The elongate member is capable of being bent into a shape by a user and of retaining the shape during use. The head extends from the distal portion of the elongate member. The needle carrier is disposed within the head. The actuator is at least partially disposed within the elongate member. The actuator is also coupled to the needle carrier for advancing the needle carrier out of the head. In one embodiment, the head defines an opening, the needle carrier holds a needle, and the actuator advances the needle carrier out of the opening. In addition, the head may include a needle catch having at least one opening for receiving the needle.

In various embodiments of the foregoing aspects of the invention, the elongate member may have a variable stiffness along its length. The diameter of the elongate member may vary along its longitudinal axis. For example, the elongate member may have a smaller diameter at its distal end than at its proximal end. Further, the elongate member may be a tube. The tube may have a non-uniform wall-thickness. The non-uniform wall-thickness may be at least partially due to scoring, which may be done in a spiral pattern.

In additional embodiments, the elongate member may be made of metals, alloys and plastics. The metals may be selected from nickel, copper, stainless steel, cobalt, vanadium, chromium, iron, and superelastic metallic alloys. The plastics may be selected from synthetic plastics, polyurethanes, polyester elastomers, and nylons. The external surface of the elongate member may be at least partially covered with a biocompatible material. The biocompatible material may be stainless steel, polyvinyl chloride, polytetraflouroethylene, expanded polytetrafluoroethylene, ethylene-tetrafluoroethylene, silicone, or combinations thereof.

In some embodiments of the foregoing aspects of the invention, the mechanism associated with the medical device is an imaging device, a stapling device, a biopsy device, an injection device, a cutting device or a capturing device. The adapter is adjustable relative to the elongate member. Adjustable, in these embodiments, means articulable and/or rotatable with respect to the elongate member.

In some embodiments of the foregoing aspects of the invention, the medical device is a suturing instrument. In one such embodiment, the distal portion of the elongate member defines an opening, the mechanism is a needle carrier for holding a needle, and the actuator advances the needle carrier out of the opening. In another such embodiment, the mechanism is a suturing head that extends from the adapter and defines an opening, a needle carrier for holding a needle is disposed within the head, and the actuator advances the needle carrier out of the opening. The suturing instrument may also include a needle catch disposed proximate the distal portion of the elongate member. The needle catch may include at least one opening for receiving the needle. In some embodiments of the suturing instrument, the head is adjustable with respect to the elongate member. Adjustable, in such an embodiment, means articulable and/or rotatable with respect to the elongate member.

In some embodiments of the foregoing aspects of the invention, the elongate member is capable of being bent into a second shape by the user and of retaining the second shape during use. In other embodiments, the elongate member is capable of being bent into a shape that includes one or more bends. In yet another embodiment, the elongate member is capable of bending in one or more directions.

Advantages and features of the invention disclosed herein will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1A is a schematic plan view of one embodiment of a medical device in accordance with the invention;

FIG. 4A is a partial schematic cross-sectional view of another embodiment of a medical device in accordance with the invention;

FIG. 4B is a schematic plan view of the medical device of FIG. 4A bent into a more efficient shape for a particular application.

DESCRIPTION

Figure 1B:
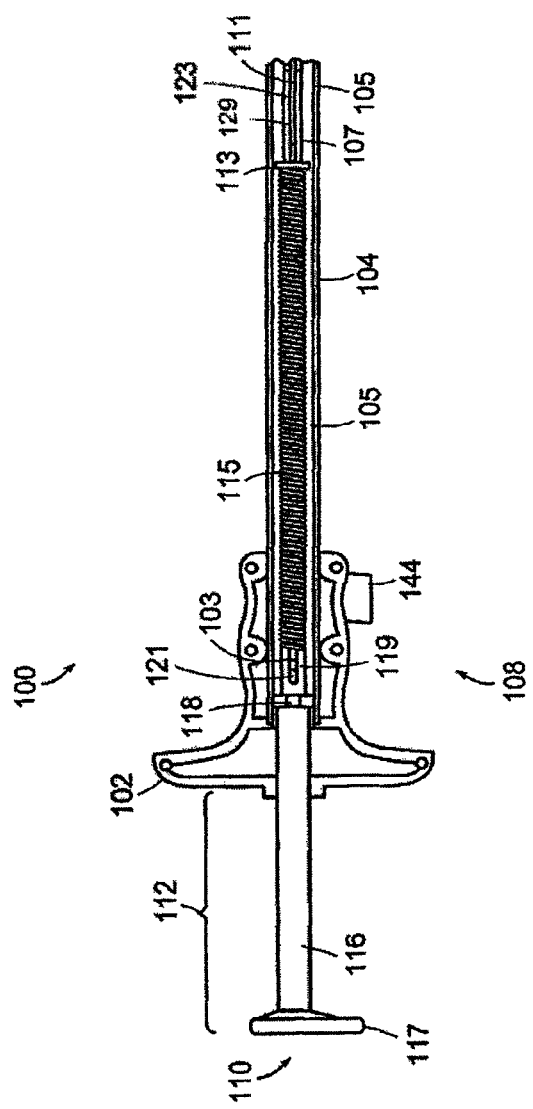
FIGS. 1B and 1C are schematic cross-sectional views of the proximal and distal portions of the medical device of FIG. 1A.

Embodiments of the invention are described below. It is, however, expressly noted that the invention is not limited to these embodiments, but rather the intention is that variations, modifications, and equivalents are included.

In accordance with one illustrative embodiment of the invention, FIG. 1A depicts a medical device 100 including an elongate member 104, a proximal portion 108, and a distal portion 106. The elongate member 104 is capable of being bent into a shape and of retaining the shape during use. The elongate member 104 enables a user to bend the device 100 into a shape to suit a specific patient need or to efficiently orient the distal portion of the device 100 to reach the location of use. The shape may include multiple bends, in multiple directions, as needed for a particular application. The device 100 maintains the shape during use. Thereafter, the elongate member 104 is capable of being bent into a second shape to suit another specific patient need or to efficiently orient the distal portion of the device 100 to reach the location of another use; the device 100 is further capable of maintaining the second shape during use. The elongate member 104 is not limited to two shapes and can be repeatedly bent into essentially any number of shapes, as necessary.

In the illustrative embodiment of FIG. 1A, the medical device 100 also includes an adapter 114 (shown in FIG. 1C) and an actuator 110. The adapter 114 is disposed at the distal portion of the elongate member 104 and is capable of coupling to a mechanism. The actuator is at least partially disposed within the elongate member 104 and is capable of coupling to the mechanism and actuating the mechanism. In the particular illustrative embodiment of FIG. 1A, the mechanism is a suturing head 109 and the medical device 100 is, therefore, a suturing instrument. Accordingly, the medical device is used for suture placement. In other embodiments, the mechanism may be an imaging device, a stapling device, a biopsy device, an injection device, a cutting device, or a capturing device.

The elongate member 104, in the depicted embodiment, is mechanically coupled to a handle 102 at the proximal portion 108. The handle 102 may take a variety of forms in various embodiments. For example, the handle 102 may be one of the types used with Boston Scientific Corporation suturing systems, in particular the Capio® Push & Catch suturing system.

The adapter 114, in the depicted embodiment, mechanically couples the distal portion of the elongate member 104 to head 109. The medical device 100 may be used with a variety of heads to suit a particular application. Examples of different types of heads are found in U.S. Pat. Nos. 6,096,051 and 6,296,608, and U.S. patent application Ser. No. 10/210,984 and 60/388,458, each of which is hereby incorporated by reference in its entirety. These types of heads can include forceps, a snare, a pair of scissors, a knife, a suturing tool, a needle, or any other mechanism, such as those previously described. Additionally, either the head 109 or the adapter 114 may be articulable or rotatable relative to the elongate member 104. For example, the adapter 114 and head may rotate about a longitudinal axis 190.

In the illustrative embodiment depicted in FIG. 1A, the actuator 110 extends longitudinally through the elongate member 104 to the distal portion 106 of the suturing instrument 100, where the actuator 110 is coupled to a needle carrier 124 (FIG. 1C) within the head 109. The actuator 110 enables the needle carrier 124 to move a needle 128 (FIG. 2A) between a retracted position and a deployed position. In the aspect of the invention depicted in FIG. 1A, the needle carrier 124 is disposed within the head 109 extending from the adapter 114 disposed at the distal portion 106 of the elongate member 104. The actuator 110 and needle carrier 124 are shown in detail in FIGS. 1B and 1C.

Referring to the illustrative embodiment of the invention depicted in FIG. 1B, the proximal portion 108 of the medical device 100 includes the handle 102, the elongate member 104, and part of the actuator 110. A suture clip 144 may be coupled to the handle 102 or the elongate member 104 to hold an end of one or more sutures prior to placement in a patient.

In the illustrative embodiment depicted in FIG. 1B, the proximal portion of the actuator 110 includes a button 117 and a shaft 116 (together 112), a bearing 118, a hole 121, a button end 119, and a wireform 103. The bearing 118 rides along a surface 105 that is formed by the inside of the elongate member 104. A wireform 103 is inserted into the hole 121, coupling it to the actuator button 117. A spring 115 encircles the wireform 103, abuts the button end 119, and is compressed between the button end 19 and a spring washer 113.

The distal portion of the actuator 110 depicted in FIG. 1B includes the spring washer 113, a center tube 107, a pusher wire 111, and a guidance sleeve 109. The spring washer 113 is seated upon the center tube 107. The center tube 107 is housed by the surface 105 and is constrained in the distal portion 106 of the medical device 100. The pusher wire 111 is attached to the wireform 103 by means of a weld, a crimp, a coupling, adhesive, or other means, and is slidably disposed within the guidance sleeve 109, the sleeve 109 being disposed within a surface 123 formed by the inside diameter of the center tube 107. In one embodiment, the pusher wire 111 is constructed of a shape memory material, such as nitinol. Nitinol is a nickel-titanium alloy. Preferably, the shape memory material is chosen for its combination of properties that allow for bendability and high column strength when constrained.

Figure 1C:
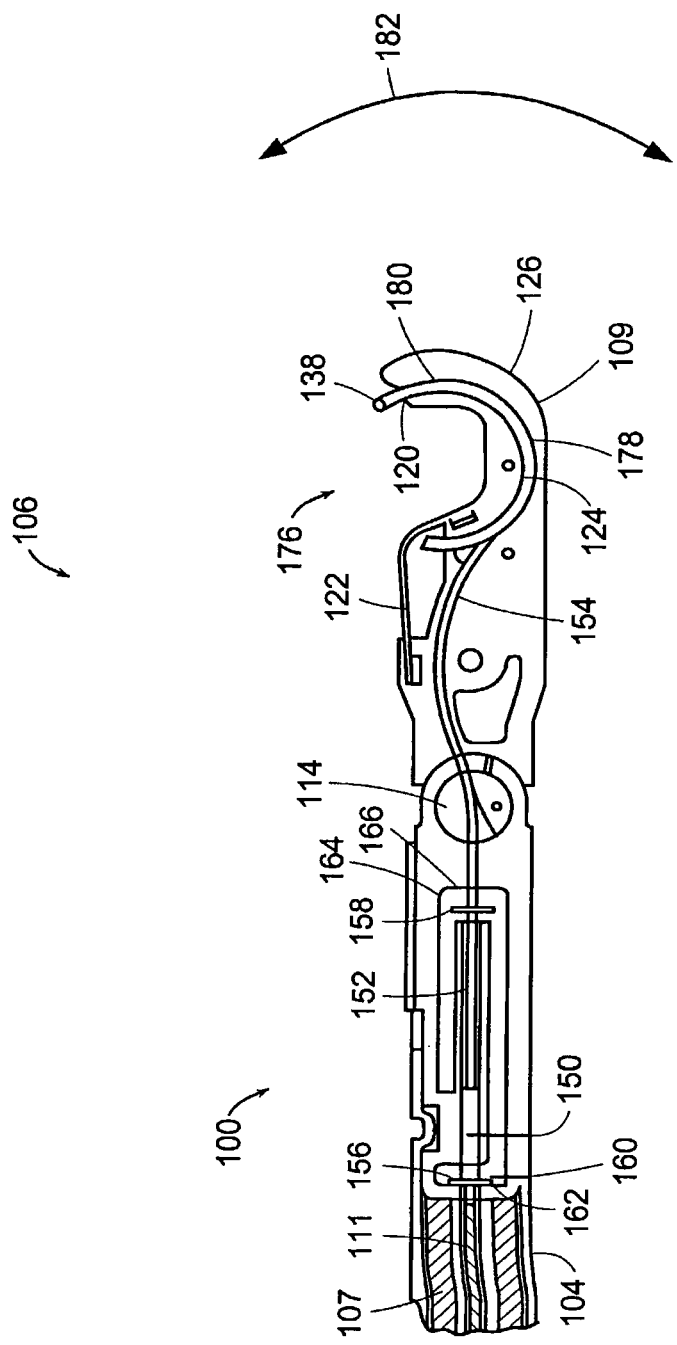

Referring to the illustrative embodiment of the invention depicted in FIG. 1C, the distal portion 106 of the medical device 100 of FIG. 1A includes the elongate member 104 and a portion of the actuator 110 coupled to the mechanism, in the form of the head 109. The portion of the actuator 110 depicted in FIG. 1C includes the pusher wire 111, a backstop washer 156, a pocket 160 that includes a back wall 162, a coupling 150, a track 152, a downstop washer 158, a pocket 164 that includes a wall 166, and a carrier wire 154. The pusher wire 111 of the actuator 110 is attached by welding or other means to the coupling 150, which is slidably disposed within the track 152. The coupling 150 is attached to the carrier wire 154, which by virtue of its attachment to the coupling 150 is also slidably disposed within the track 152. The carrier wire 154 is mechanically coupled to the extendable needle carrier 124 by means of a weld, a coupling, adhesives, or other means. The coupling 150 abuts the backstop washer 156 that is slidably disposed about the pusher wire 111 and is contained within the pocket 160 that includes the back wall 162, against which the backstop washer 156 rests. The track 152 terminates distally in the pocket 164 that includes the wall 166. The downstop washer 158 is slidably disposed about the carrier wire 154 and constrained within the pocket 164.

In some illustrative embodiments, such as depicted in FIG. 1C, the medical device 100 includes an adapter 114 that couples the distal portion of the elongate member 104 to a mechanism (for example, the head 109 in FIG. 1C). In one embodiment, the adapter 114 includes an articulation device. The articulation device facilitates the rotation (in the directions indicated by arrow 182) and positioning of the mechanism. The articulation device may, in conjunction with the shape of the elongate member 104 established by the user, facilitate access to deep and/or difficult to reach areas within the patient. The adapter 114 may also be fixed or articulate with respect to the elongate member 104. The adapter 114 may also be a threaded coupling, a clevis, or some other type of mechanical coupling device. Alternatively, the instrument 100 may not include an adapter 114 for a mechanism, as illustrated in FIGS. 4A and 4B.

In the exemplary embodiment depicted in FIG. 1C, the mechanism is a suturing head 109. The head 109 defines an opening 120 through which the needle carrier 124 advances the needle 128. The head 109 includes a curved portion 126, the needle carrier 124, and a needle catch 122. The curved portion 126 defines a channel 178, which ends with the opening (or needle exit port 120). The curved portion 126 also defines an opening 176 for receiving tissue. The needle carrier 124 is disposed within the channel 178 in the curved portion 126. A distal portion 180 of the needle carrier 124 defines a lumen 138 for holding the needle 128. The exact structure and operation of the head 109 varies based on the type of head used.

Figure 2A:
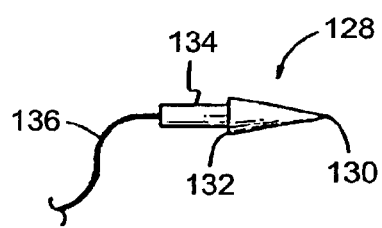
FIG. 2A is a schematic plan view of a needle coupled to a suture for use in a suturing instrument in accordance with the invention.

Referring to FIG. 2A, in one illustrative embodiment, the needle 128 includes a tip 130 and a shaft 134 coupled to the tip 130, thereby forming a shoulder 132. The shaft 134 is coupled to a suture 136. The needle 128 is inserted into the lumen 138 and held by a slight friction fit. The suture 136 extends out of the medical device 100.

In operation, a user (such as a physician or other medical personnel) first determines an appropriate shape for the elongate member 104 to suit a specific patient need or to efficiently orient the distal portion of the medical device to reach the location of use. The shape may include bends in multiple directions and/or in multiple places. The user may bend the elongate member into the desired shape with his hands. In various embodiments of the invention, no tool is necessary to bend the elongate member 104. Alternatively, the user may use a fixture to create the desired shape. The use of a fixture may enable the user to repeatedly duplicate a particular shape. During use, the elongate member 104 retains the shape established by the user. The elongate member 104 of the medical device 100 has enough column strength to withstand operational forces without substantial distortion. The components of the actuator 110 are sized and their materials are selected such that the actuator 110 will not bind when the elongate member 104 is bent. An alternative actuator design is explained in detail with respect to FIG. 3.

Figure 2B:
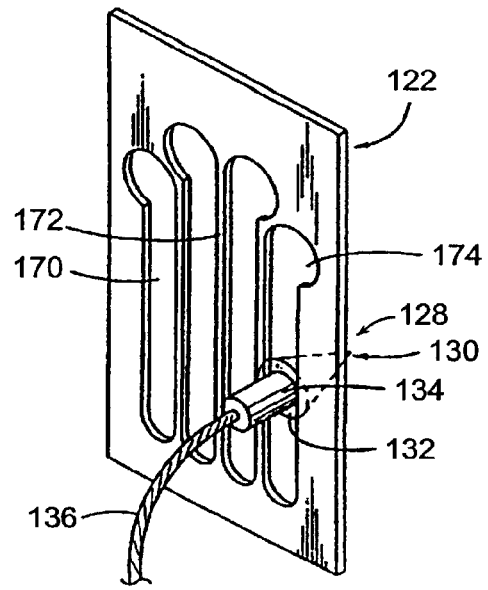
FIG. 2B is a schematic perspective view of a needle catch for use with the suturing instrument of FIG. 1A.

In the next step in the operation of the medical device, the user positions the distal portion of the device at the location of use and actuates the actuator. In the illustrative embodiment of FIGS. 1A, 1B, and 1C, the medical device 100 is a suturing instrument, the distal portion of which is placed at the suturing location and actuated. Referring again to FIGS. 1B and 1C, actuation is accomplished by pushing on the button 117, which is attached to the pusher wire 111 via the wireform 103. The pusher wire 111 moves the coupling 150 along the track 152 concomitantly moving the carrier wire 154, which slidably moves the needle carrier 124 through the needle exit port 120. The user continues to push the button 117 until the needle 128 enters the needle catch 122. The needle catch 122, as shown in FIG. 2B, includes openings 170 defined by successive ribs 172. The needle catch 122 receives the needle 128 (coupled to the suture 136) through opening 170, the ribs 172 deflect slightly to allow the needle 128 to pass through. After the formed shoulder 132 has passed the ribs 172, the ribs 172 spring back to their original position defining the openings 170, and the needle 128 remains captured in the needle catch 122. The needle 128 and the needle catch 122 shown are merely one possible type and other designs may be chosen.

Still describing the operation of an exemplary suturing instrument with respect to FIGS. 1B and 1C, when the user releases the button 117, the spring 115 urges the button 117 proximally, moving the pusher wire 111, the coupling 150, the carrier wire 154, and the needle carrier 124 proximally along with the button 117 to the retracted position. As the needle carrier 124 moves back to the retracted position, the needle 128 slides out of the lumen 138. The openings 170 (shown in FIG. 2B) are chosen to be smaller in dimension than the formed shoulder 132 (shown in FIG. 2A). This causes the needle catch 122 (shown in FIG. 1C and FIG. 2B) to retain the needle 128, because the flat rear surface of the shoulder 132 prevents the needle 128 from passing back through the opening 170. When it is necessary to remove the needle 128 from the needle catch 122, the needle 128 may be moved toward an enlarged portion 174 (shown in FIG. 2B) of opening 170. The enlarged portion 174 is sized to allow the formed shoulder 132 to pass through without resistance. The needle catch 122 may be constructed of thin stainless steel of high temper, such as ANSI 301 full hard. The needle catch 122 may be fabricated by way of stamping, laser machining, or chemical etching.

Preferably, the component materials of the medical device are biocompatible. For example, components of the medical device, such as the handle 102 and portions of the actuator 110, may be fabricated from extruded, molded, or machined plastic material(s), such as polypropylene, polycarbonate, or glass-filled polycarbonate. Other components, for example, such as the mechanism, may be made of stainless steel. Other suitable materials will be apparent to those skilled in the art. Preferably, in embodiments in which the medical device is a suturing instrument, the material(s) used to form the suture are also biocompatible. The user selects the length, diameter, and characteristics of the suture to suit a particular application.

Additionally, mechanical components and operation such as those disclosed in U.S. Pat. Nos. 5,364,408 and 6,048,351, each of which is incorporated by reference herein in its entirety, may be employed with features of the invention.

Figure 3:
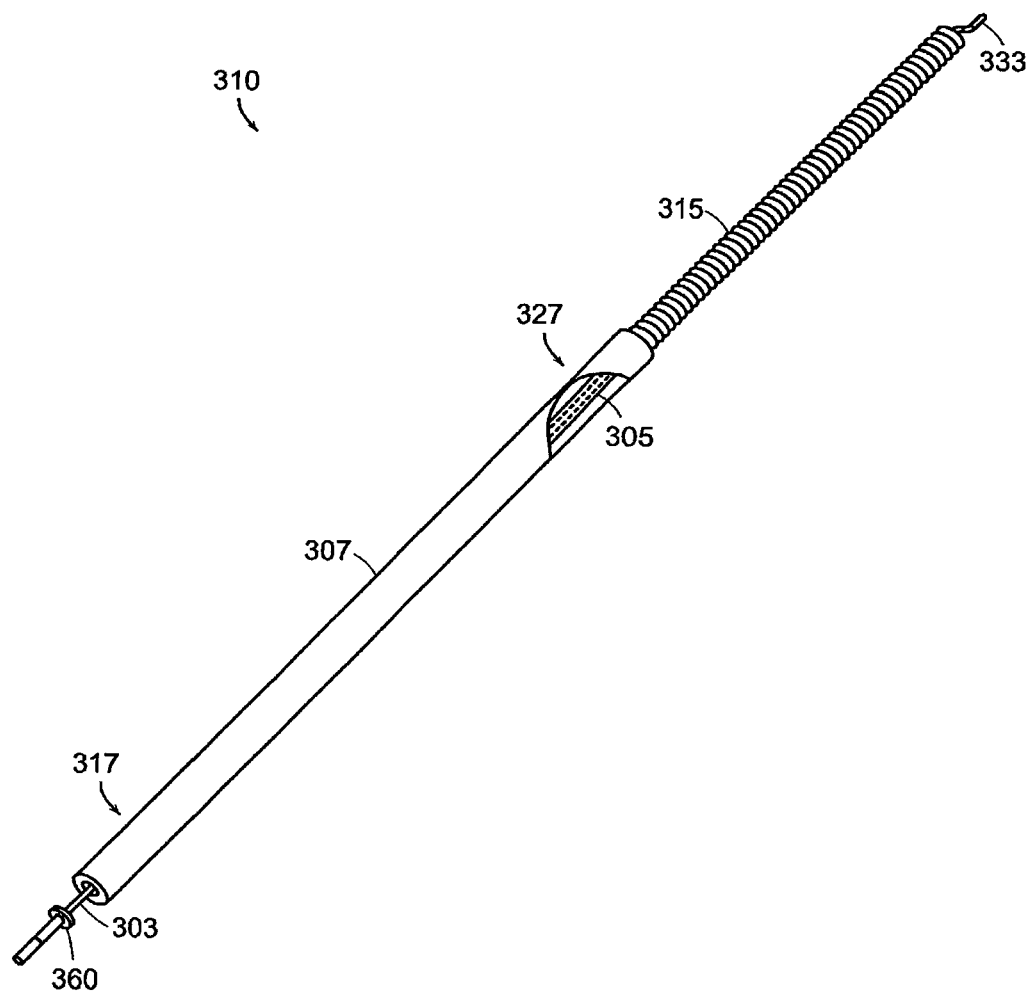
FIG. 3 is a schematic view of a portion of an alternative actuator for use in a medical device in accordance with the invention.

FIG. 3 is a schematic view of a portion of an alternative actuator for use with a medical device in accordance with the invention, such as that shown in FIG. 4A. The actuator 310 includes a wireform 303 with a contact form 333 at its proximal end, a spring 315, a spring tube 305, and a center tube 307. In one embodiment, the wireform 303 is constructed of stainless steel. In another embodiment, the wireform 303 is constructed of nitinol. The contact form 333, which is a Z form of the wireform 303 in some embodiments, is mechanically coupled to a shaft (not shown, but similar to the shaft 116 in FIG. 1B). The wireform 303 extends longitudinally through the spring tube 305 and the center tube 307 and out of the distal end 317 of the center tube 307. The spring tube 305 extends longitudinally through the spring 315 and into the proximal end 327 of the center tube 307. Preferably, in comparison to the spring 315, the center tube 307 has a thick wall. In one embodiment, the thick wall of the center tube 307 prevents the spring 315 from entering the center tube 307. In another embodiment, the fact that the center tube 307 has an inner diameter that is smaller than the outer diameter of the spring 315 prevents the spring 317 from entering the center tube 307. In some embodiments of the invention that incorporate the actuator depicted in FIG. 3, the wireform 303 is attached to a pusher wire (not shown, but similar to the pusher wire 111 in FIGS. 1B and 1C) by means of a weld, a crimp, a coupling, adhesive or other means. In such embodiments, the actuator may further include a washer 360 to prevent the attachment from entering the distal end 317 of the center tube 307. In some embodiments in which the medical device is a suturing instrument, the pusher wire 311 is mechanically coupled to an extendable needle carrier (not shown, but similar to the needle carrier 124 of FIG. 1C). In other embodiments in which the medical device is a suturing instrument, the wireform 303 is directly mechanically coupled to the extendable needle carrier.

In response to the contact form 333 being pressed, for example, by a button (not shown, but similar to the button 117 of FIG. 1B), the spring 315 compresses against the proximal end 327 of the center tube 307 and the distal end of the spring tube 305 travels within the center tube 307 toward the distal end 317 of the center tube 307. The distance of travel, in one illustrative embodiment, is about 0.5 inch to about 1.0 inch. The deflection of the wireform 303 is limited by the spring 315, the spring tube 305, and the center tube 307, as it travels toward the distal end 317 of the center tube 307. The wireform 303 in some embodiments, or the pusher wire in other embodiments, actuates the mechanism relative to the elongate member. For example, in some embodiments of the medical device as a suturing instrument, such as described with respect to FIGS. 1B and 1C, the wireform 303 advances a needle via the needle carrier to the needle catch.

The components of the actuator 310 are sized and their materials are selected such that the actuator 310 will not bind when the elongate member (not shown, but similar to the elongate member 104 of FIGS. 1B and 1C) is bent. The center tube 307, the spring tube 305, the spring 315, and the wireform 303 are flexible components. When the elongate member is bent, the components inside bend with it. The outer diameter of the center tube 307 is preferred to be close to the inner diameter of the elongate member to prevent kinking. In some embodiments, the bent elongate member holds the center tube 307 stationary. In some embodiments, the clearance between the center tube 307 and the spring tube 305 is ample to allow the spring tube 305 to travel even when the center tube 307 is bent. The outer diameter of the spring 315, in some embodiments, is much smaller than the inner diameter of the elongate member 304 thereby allowing the spring 315 to move when the elongate member 304 is bent. The spring 315 is also located in a position within the elongate member where the elongate member is less likely to be bent.

In accordance with another illustrative aspect of the invention, FIG. 4A depicts a medical device 400 including an elongate member 404, a mechanism, and an actuator 410. In the particular illustrative embodiment of FIG. 4A, the medical device 400 is a suturing instrument and the mechanism is a needle carrier 424. The elongate member 404 includes a distal portion 406. In the specific embodiment depicted in FIG. 4A, the elongate member 404 also defines an opening 420. Like the elongate member 104 depicted in FIG. 1A, the elongate member 404 depicted in FIG. 4A is capable of being bent into a shape and of retaining the shape during use. The mechanism is disposed at the distal portion 406 of the elongate member 404. The needle carrier mechanism 424, in particular, is designed to hold a needle 428. The actuator 410 is at least partially disposed within the elongate member 404 and coupled to the mechanism for actuating the mechanism relative to the elongate member 404. In the specific embodiment depicted in FIG. 4A, the actuator 410 is coupled to the needle carrier mechanism 424 for advancing the needle 428 out of the opening 420.

FIG. 4B is a view of the medical device 400 of FIG. 4A bent into a shape for a particular application. The needle 428 in FIG. 4B is partially advanced out of the opening 420 by the needle carrier mechanism 424. The shape of the elongate member 404 in FIG. 4B features a first bend 450 and a second bend 470. Although the first bend 450 and the second bend 470 are both smooth, shallow curves, the first bend 450 is sharper than the second bend 470. A section 460, between the first bend 450 and the second bend 470, is generally straight. As shown in FIG. 4B, the outer surface of the distal portion 406 of the elongate member 404 has been scored in a spiral pattern. The scoring may be done to increase the bendability of the distal portion 406 of the elongate member 404.

Figure 5A:
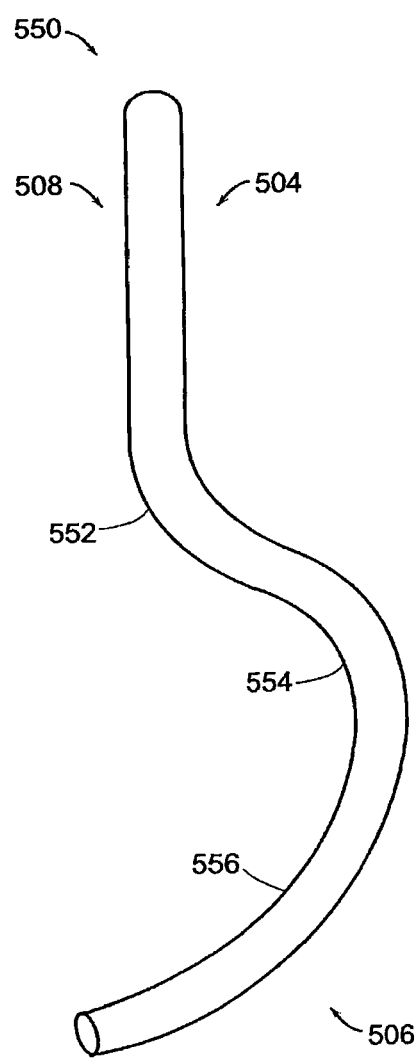
FIGS. 5A and 5B are schematic perspective views of an exemplary elongate member bent into a first and a second shape, respectively.
Figure 5B:
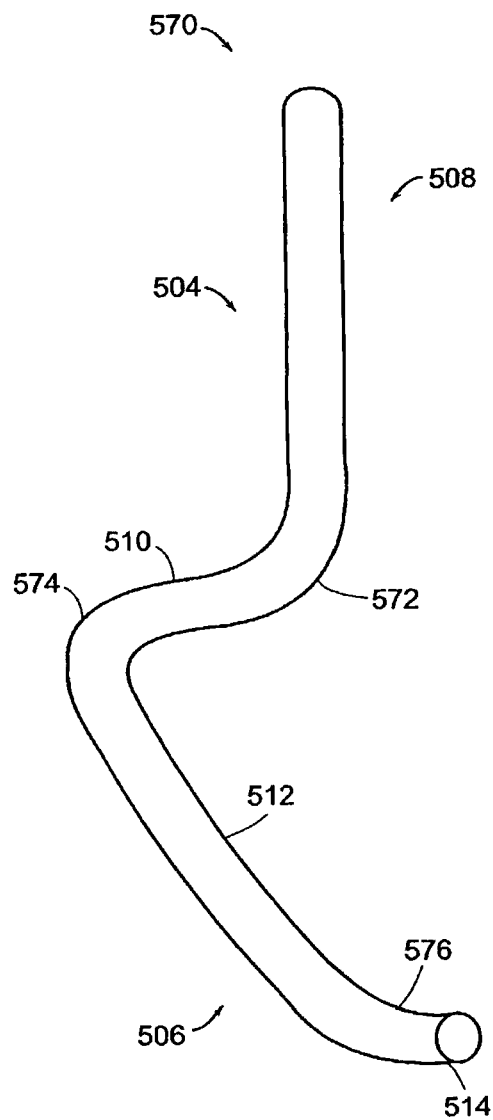

FIGS. 5A and 5B depict an elongate member 504, such as described with respect to FIGS. 1A-1C and FIGS. 4A-4B, bent into a first shape 550 and a second shape 570. The elongate member depicted in FIGS. 5A and 5B is generally tubular and has a proximal end 508 and a distal end 506. The first shape 550 includes a first bend 552, a second bend 554, and a third bend 556. The first bend 552 forms an obtuse angle in the elongate member 504. The first bend 552 is also sharper than the second bend 554, which is sharper than the third bend 556. The third bend 556 may best be described as a gentle curve. The first bend 552, second bend 554, and third bend 556 are all coplanar. The second shape 570 includes a first bend 572, a second bend 574, and a third bend 576. The second bend 574 is sharper than the first bend 572, which is sharper than the third bend 576. The second bend 574 forms an angle less than 90.degree. in the elongate member 504. Each bend 572, 574, 576 in the second shape 570 has a completely different orientation than the other bends. The proximal portion 508 of the elongate member 504 in the second shape 570 is coplanar with a section 510 of the elongate member 504 between the first bend 572 and the second bend 574. However, a section 512 of the elongate member 504 between the second bend 574 and the third bend 576 does not fall within the same plane as the proximal portion 508, because the second bend 574 is rotated out of the plane of the first bend 572. Similarly, a section 514 of the elongate member 504 on the opposite side of the third bend 576 with respect to section 512 does not fall within the same plane as section 510 because the third bend 576 is rotated out of the plane of the second bend 574.

Portions of the elongate member 504 may remain straight for a particular use. For example, the proximal end of the elongate member 504 may remain unbent for a particular use as depicted in FIGS. 5A and 5B. In fact, the elongate member 504 need not be bent at all for a particular application. When the elongate member 504 is bent for a particular application, it need not been bent in the same location or locations that it has previously been bent. The elongate member 504 may have more or less than three bends for a particular application. Further, all bends may be similarly oriented for a particular application. For example, a user may want the elongate member to be shaped into an arc.

In various embodiments of the foregoing aspects of the invention, the elongate member 504 depicted in FIGS. 5A and 5B may have a variable stiffness along its length. The proximal end 508 may be stiffer than the distal end 506 of the elongate member 504, because it is more likely that the distal end 506 will require bending. The diameter of the elongate member 504 may vary along its longitudinal axis. Having a smaller diameter at, at least one point along the longitudinal axis of the elongate member 504 may allow the elongate member 504 to bend more easily at that point. The elongate member 504 may have a smaller diameter at its distal end 506 than at its proximal end 508. The smaller diameter at the distal end 506 of the elongate member 504 may allow the elongate member 504 to be used in smaller openings in the human body. In various embodiments of the foregoing aspects of the invention, the elongate member 504 may have a non-uniform wall-thickness. The non-uniform wall-thickness, in some embodiments, is achieved by material selection. The wall thickness, in other embodiments, is thinned at various locations along the length of the elongate member 504 to make the elongate member 504 easier to bend where the wall is thinner. The non-uniform wall thickness may be at least partially due to etching. The non-uniform wall-thickness may be at least partially due to scoring. Etching or scoring may be done in lines parallel or transverse to the longitudinal axis of the elongate member 504, in a spiral pattern, or in another pattern. The inner surface of the elongate member 504, the outer surface of the elongate member 504, or both surfaces may be etched or scored. Spiral scoring, for example, may allow the elongate member 504 to bend more easily without kinking. Other means of and approaches to modifying wall thickness will be obvious to those of skill in the art.

In various embodiments of the invention, the elongate member 504 depicted in FIGS. 5A and 5B may have a variety of surface characteristics. For example, one embodiment of the elongate member 504 has an entirely smooth outer surface. Another embodiment may have an outer surface that is at least partly rough. Scoring or etching the surface of the elongate member 504 may, for example, cause the roughness. Roughness may be undesirable due to the possibility of interaction with human tissue during use or due to a greater difficulty in cleaning the instrument. Roughness on the outer surface of the elongate member 504 may be avoided, where necessary, by thinning the wall thickness from the inner surface of the elongate member 504. Alternatively, covering at least some of the rough surface areas with a smooth material may alleviate any potential problems due to roughness on the outer surface of the elongate member 504.

An elongate member 504, such as those depicted in FIGS. 5A and 5B and used in medical devices exemplified by FIGS. 1A-1C and FIGS. 4A-4B, can have essentially any cross-sectional shape. Such cross-sectional shapes include polygonal, arcuate, or combinations of polygonal and arcuate elements. In the present application, the term polygonal is used to denote any shape including at least two line segments, such as rectangles, trapezoids, and triangles. Examples of arcuate shapes include circular and elliptical. FIGS. 5A and 5B specifically depict an elongate member 504 with a circular cross-section and generally cylindrical shape according to one embodiment of the invention. The elongate member 504 may, for example, have a tubular shape.

In various embodiments of the foregoing aspects of the invention, the elongate member is made of metals, alloys, or plastics or a combination thereof. Metals that can be used to form the elongate member include: nickel, copper, stainless steel, cobalt, vanadium, chromium, iron, and superelastic metallic alloys. Plastics that can be used to form the elongate member include synthetic plastics, polyurethanes, polyester elastomers, and nylons. In embodiments in which the elongate member itself is not necessarily made of a biocompatible material, the external surface of the elongate member may be at least partially covered with a biocompatible material. In embodiments with a particularly long elongate member, for example, the proximal portion of the elongate member is made of or covered with a biocompatible material. The entire external surface of the elongate member of other embodiments may be made of or covered with a biocompatible material. The biocompatible material may be stainless steel, polyvinyl chloride, polytetraflouroethylene, expanded polytetraflouroethylene, ethylene-tetrafluoroethylene, silicone, or other suitable material. In some embodiments, the external surface of the elongate member is at least partly plated or spray coated with a biocompatible material. In other embodiments, other techniques, such as heat-shrinking, are used to apply the biocompatible material. Other materials and application techniques can be used.

The elongate member 504 described above can be combined with a variety of actuators and mechanisms to form a variety of medical devices. Such medical devices include, but are not limited to, imaging devices, stapling devices, biopsy devices, injection devices, cutting devices, and capturing devices, as used in endoscopic procedures.

Other embodiments incorporating the concepts disclosed herein are within the spirit and scope of the invention. The described embodiments are to be considered in all respects as only illustrative and not restrictive.

What is claimed is:

1. A medical device comprising:
a handle;
an elongate member extending from the handle and capable of being bent into a shape by a user along its entire length and having variable stiffness, the elongate member having a proximal portion and a distal portion, the elongate member comprising a first tube; and
an actuator at least partially disposed within the proximal portion of the elongate member and comprising mechanical linkage that extends longitudinally through the elongate member to the distal portion, the actuator comprising a spring, a second tube, and a third tube, each capable of being bent when the elongate member is bent, the second tube disposed adjacent to a distal end of the spring, the third tube at least partially longitudinally extended through each of the spring and the second tube, the third tube spaced apart from an inner surface of the second tube when unbent, the third tube being slideable within the second tube when the second tube is bent.

2. The medical device of claim 1, wherein the distal portion of the elongate member has a greater bendability than the proximal portion of the elongate member.

3. The medical device of claim 1, wherein the elongate body member is capable of retaining the shape during use.

4. The medical device of claim 1, further comprising:
a needle carrier holding a needle, the needle carrier is mechanically coupled to the actuator for advancing the needle out of an opening defined by the distal portion of the elongate member.

5. The medical device of claim 4, further comprising:
a needle catch defining at least one opening disposed on the elongate member.

6. The medical device of claim 5, wherein the needle catch is configured to receive the needle through the at least one opening and retain the needle after the needle carrier is retracted.

7. The medical device of claim 1, wherein the first tube includes a spiral cut.

8. The medical device of claim 1, wherein the elongate member comprises a material selected from the group consisting of metals, alloys, and plastics.

9. The medical device of claim 8, wherein the metal is selected from nickel, copper, stainless steel, cobalt, vanadium, chromium, iron, and super elastic metallic alloys.

10. The medical device of claim 8, wherein the plastics are selected from synthetic plastics, polyurethanes, polyester elastomers, and nylons.

11. The medical device of claim 1, wherein an external surface of the elongate member is at least partially covered with a biocompatible material.

12. The medical device of claim 1, wherein the elongate member is capable of bending in one or more directions.

13. A medical device comprising:
a handle;
an elongate member extending from the handle and capable of being bent into a shape by a user along its entire length and having variable stiffness, the elongate member having a proximal portion and a distal portion, the elongate member comprising a first tube;
an actuator at least partially disposed within the proximal portion of the elongate member and comprising a mechanical linkage that extends longitudinally through the elongate member to the distal portion, the actuator comprising a spring, a second tube, a third tube, and a wireform, each capable of being bent when the elongate member is bent, the second tube disposed adjacent to a distal end of the spring, the third tube at least partially longitudinally extended through each of the spring and the second tube, the third tube spaced apart from an inner surface of the second tube when unbent, the third tube being slideable within the second tube when the second tube is bent, the wireform at least extending longitudinally within the second tube and the third tube and out of a distal end of the second tube;
the wireform mechanically coupled to an extendable needle carrier for advancing the needle carrier out of an opening defined by the distal end of the elongate body, the needle carrier holding a needle.

14. The medical device of claim 13, wherein the distal portion of the elongate member has a greater bendability than the proximal portion of the elongate member.

15. The medical device of claim 13, wherein the elongate body member is capable of retaining the shape during use.

16. The medical device of claim 13, further comprising:
a needle catch defining at least one opening disposed on the elongate member.

17. The medical device of claim 16, wherein the needle catch is configured to receive the needle through the at least one opening and retain the needle after the needle carrier is retracted.

18. The medical device of claim 13, wherein the first tube includes a spiral cut.

19. The medical device of claim 13, wherein the elongate member comprises a material selected from the group consisting of metals, alloys, and plastics.

20. The medical device of claim 19, wherein the metal is selected from nickel, copper, stainless steel, cobalt, vanadium, chromium, iron, and super elastic metallic alloys.

21. The medical device of claim 19, wherein the plastics are selected from synthetic plastics, polyurethanes, polyester elastomers, and nylons.

22. The medical device of claim 13, wherein the elongate member is capable of bending in one or more directions.

* * * * *